United States Patent [19]
Lee et al.

[11] Patent Number: 5,183,658
[45] Date of Patent: Feb. 2, 1993

[54] HANTAAN VIRUS STRAIN ROK84/105 AND VACCINE THEREFOR

[75] Inventors: Ho W. Lee; Sun J. Riu, both of Seoul; Chang N. An, Suwon, all of Rep. of Korea

[73] Assignee: Korea Green Cross Corporation, Rep. of Korea

[21] Appl. No.: 438,327

[22] Filed: Nov. 16, 1989

[30] Foreign Application Priority Data

Nov. 18, 1988 [KR] Rep. of Korea ............... 15199/1988

[51] Int. Cl.$^5$ .......................... A61K 39/12; C12N 7/00
[52] U.S. Cl. ......................................... 424/89; 424/88; 435/235.1; 435/236; 435/238; 435/239
[58] Field of Search ................. 424/89, 88; 435/235.1, 435/236, 238, 239

[56] References Cited

PUBLICATIONS

H. W. Lee, "Korean Hemorrhagic Fever", *Ebola Virus Hemorrhagic Fever*, Copyright 1988, Elsevier North Holland Biomedical Press, S. R. Pattyn Editor, pp. 331-343.

H. W. Lee, "Korean Hemorrhagic Fever", Progress in Medical Virology, Copyright 1982, S. Karger (publishers) Basel, Switzerland, vol. 28, pp. 96-113.

H. W. Lee, 1982, "Hemorrhagic Fever with Renyl Syndrome (HFRS)", Scand. J. Infect, Dis. Suppl. 36:82-85.

H. W. Lee et al., 1980, "Management of Korean Hemorrhagic Fever", Medical Progress, Sep. issue, pp. 15-21.

Reference Document (Author or Authors unknown), published before Dec. 28, 1989, p. 345.

Yamanishi et al, *Vaccine*, vol. 6, pp. 278-282, Jun. 1988.

Lee et al, *Biological Abstracts*, Oct. 15, 1978 Ref. #46752.

French et al, *Science*, vol. 211, pp. 1046-1048, Mar. 6, 1981.

Hamada et al, *Biological Abstract*, vol. 81(8), 1986, Ref. #73451.

Lee et al, *The Journal of Infectious Disease*, vol. 146, No. 5, pp. 638-644, Nov. 1982.

*Primary Examiner*—Johnnie R. Brown
*Assistant Examiner*—Abdel A. Mohamed
*Attorney, Agent, or Firm*—Merchant, Gould, Smith, Edell, Welter & Schmidt;

[57] ABSTRACT

The present invention relates to Hantaan virus and a vaccine therefor. The Hantaan virus vaccine can be prepared as follows: The Hantaan virus ROK84/105 strain isolated from the human body as a seed strain, injected to one-day-old suckling mouse or rat, which is raised for about 10 days. Thereafter, the head of the mouse or rat is cut apart after paralyzing the mouse or rat to take the brain, the brain is treated with ethyl alcohol and protamine sulfate solution, the resultant is purified and inactivated, and an adjuvant is added to the final product.

15 Claims, 5 Drawing Sheets

-LOG ICR MOUSE $LD_{50}$/mL 9.59

DAYS AFTER INOCULATION (HANTAAN VIRUS VACCINE MIXED WITH 0.05% OF FORMALIN)

HANTAAN VIRUS STRAIN ROK84/105 AND VACCINE THEREFOR

FIELD OF THE INVENTION

The present invention relates to the novel Hantaan virus ROK84/105 strain, a pathogen of hemorrhagic fever with renal syndrome, and vaccine of Hantaan virus having an excellent effect in preventing the hemorrhagic fever with renal syndrome utilizing the above virus.

DESCRIPTION OF THE PRIOR ART

It has been known that there are about 10 or more types of epidemic hemorrhagic fever caused by virus on the earth, and these syndromes are classified into mosquitoborne, tickborne and zoonotic, while epidemic hemorrhagic fever of the Korean type caused by the Hantaan virus strain of the present invention belongs to zoonotic. The pathogen of this hemorrhagic fever of the Korean type has not been isolated, but only the conjecture that it should be correlates to the mouse is prevalent, while it has not been proved what kind of host and what kind of pathogen it has. There were various conjecture about the natural host of epidemic hemorrhagic fever, but nothing has been proved yet. Asanuma et al. deduced that the epidemic hemorrhagic fever could be caused by inoculating the emulsion of Trombicular mite, a parasite of *Apodemus agrarius coreae* and suggested that the mite might be the host or the carrier for the disease.

The present inventors successfully isolated the pathogen for the disease from the lung and kidney tissue of *Apodemus agrarius coreae* caught at Dongduchun, Korea where the hemorrhagic fever of Korean type was prevalent. The pathogen thus obtained was identified as virus, and it was named "Hantaan virus". The patients of hemorrhagic fever caused by the virus has appeared not only in Korea but also in other areas of the world, the symptoms of the patients of other areas being similar to that of the Korean patients.

The present inventors proved that there were fluorescent antibodies against the above virus in the serum of the patients of hemorrhagic nephrosonephritis of the Russia, the nephropathia epidemics of Finland, and the epidemic hemorrhagic fever of Japan, whose disease is caused by Hantaan virus or virus having antigenic similarity. Therefore, the World Health Organization (WHO) nominated those sorts of disease "hemorrhagic fever with renal syndrome".

The symptoms of Hantaan virus-infected patient mostly start with elevation of body temperature to 37° to 38° C., chill, headache, nervous breakdown and muscular aches, accompanied by upper respiratory infective symptoms such as cough, pharyngal ache, snivel and the like for 3 to 5 days and followed by severe dyspnea, pain of the chest and blood phlegm with the progress of seriousness. In rare severe cases, peculiar red-faced hemorrhage layers appear in skin or conjunctiva, the patient possibly being led to death by this respiratory virus infection.

The present inventors carried out an extensive research with a view toward eliminating the above-described disease. As a result, the present inventors successfully detected the pathogen causing the above-described disease and prepared a vaccine for preventing or inhibiting infection utilizing the said virus.

SUMMARY OF THE INVENTION

Accordingly, an object of the present invention is to provide an economical and efficient method for mass production of Hantaan virus vaccine.

Another object of the present invention is to provide a novel Hantaan virus strain, utilized practically in the above-described method.

Other objects, features and advantages of the present invention will hereinafter become more readily apparent from the following detailed description.

DETAILED DESCRIPTION OF THE PREFERRED EMBODIMENT

The present inventors succeeded in 1984 in collecting serum of the patient showing epidemic hemorrhagic fever who was a soldier serving at Paju, Kyungkido, Rep. of Korea on the third day from the day when he was taken ill. Then, the present inventors were successful in isolating the virus by culturing fourth series of generation culture in Vero E6 cell. A petition for deposit of this virus was submitted to Korean Depository, Korean Federation of Culture Collections of Microorganisms(KFCC) on Nov. 9, 1989, but the deposit was refused on the ground that the virus is pathogenic. And therefore, the present inventors deposited the present virus with American Type Culture Collection, Rockville, Md. 20852 on Oct. 12, 1989, in order to file a patent application with the United States Patent and Trademark Office. The viability of the virus culture was tested on Feb. 1, 1990 and found to be viable and the virus was assigned the ATCC designation VR 2250. The present inventors titled this virus "Hantaan virus ROK84/105" and used this virus as the seed of Hantaan virus vaccine.

In general, a vaccine to be administered to human should be desirably consist of strains originated from a human body, and the Hantaan virus collected from the blood of a human body is not only well proliferated in the brain of mice or rats, but also contains large quantities of the antigens suitable for the preparation of vaccine, so that they should be most suitable for attaining the above mentioned objects through the utilization of mice or rats.

If the virus according to the present invention is to be classified, it belongs to Hantaan virus of the four types of hantavirus genus of Bunyaviridae family; Hantaan Virus (prototype 76–118), Seoul (Virus (prototype 80-39), Prospect hill Virus and Pumala Virus. This virus is collected from the blood of patient which is attacked with hemorrhagic fever with renal syndrome, and it is proliferated in the brains of mice or rats.

The present inventors the first attained the growth, proliferation and isolation of this virus, and the cell used for isolating this virus was Vero E6 cell which was obtained from ATCC (deposit number:C 1008, CRL 1586) and Infectious Disease Research Laboratory of American Military, and was multiplicated in a tissue culture media.

The tissue culture media consisted of 95% of Eagle media and 5% of fetal calf serum(FCS). The blood of virus-infected patient was added to the tissue culture cells, and it was cultured in the $CO_2$-incubator at 36° C., and then the proliferation of virus was detected by the indirect immunofluorescent assay. In the first series of generation culture, there was no proliferation of virus, but the fourth series of generation culture showed that the antigen of the virus was identified by fluorescent spot in the protoplast of the cell. This virus was inoculated into the brain of suckling mouse or rat in order to examine whether proliferation of virus was made or not. As a result of this experiment, it was confirmed that the virus multiplicated uniquely proliferated in the brain of suckling mouse or rat.

The present inventors established that Hantaan virus ROK84/105 of the present invention could be produced in a mass production from the brains of suckling mice or suckling rat, and also established extraction and purification methods thereof. The Hantaan virus ROK84/105 strain was stabilized at pH 7.2 and at 4° C., the stabilized virus was inoculated in the brain of mouse, and a brain suspension was prepared by 20% of phosphate buffer(pH 7.2), with the result that the titer of the antigen was over 8,192 when measured by the enzyme linked immunoabsorbent assay(ELISA).

The yields of Hantaan virus ROK84/105 of the invention was much higher than that of other virus such as Hantaan virus 76-118 strain.

As a result of carrying out an extensive research on proliferation of the Hantaan virus under the above-described condition, the present inventors found that Hantaan virus ROK84/105 of this invention was capable of providing the sufficient amount of antigen for the preparation of a Hantaan virus vaccine, and that the formation of the antibody is markedly superior.

The virus of the invention should be more suitable for manufacturing a vaccine for use in the human body compared with the Hantaan virus prototype 76-118 derived from *Apodemus agrarius coreae,* in view of the fact that the former is derived form the human body.

The Hantaan virus ROK84/105 strain of the invention has the physico-chemical characteristics, i.e., the characteristics of Bunyaviridae as specified below:

1. virion particle sphere or ellipsoid, diameter about 95 nm, RNA 2. envelope surrounded lipoprotein envelope and projecting a number of fibers of 5-10 nm.

3. Structure

.single stranded
.Three-segment
.Negative-sense RNA genomes
.Total molecular weight: $4.5 \times 10^6$ .Three viral nucleocapsids
.Two virus-specified glycoprotein 4 Multiplication of virus cytoplasm of infected cell 5. characteristics The novel Hantaan virus ROK84/105 strain of the invention has the following unique characteristics in comparing with that of the known Hantaan virus 76-118 strain.

1) The titer of the virus in Vero E6 cell is $10^{7.2}$/ml.
2) The titer of the virus in the brain of the suckling mouse is $10^{9.8}$/ml.
3) The titer of the virus in the brain of suckling rat is $10^{9.3}$/ml.

* As shown above, this virus has a strong pathogenecity in rat or mouse, the mice or råts dying between 7th and 12th day after injection.

4) When this virus is inoculated to an ICR suckling mouse, proliferation of virus is faster than the other viruses, and the antibody appears from fifth day after inoculation, its quantity amounting to more than 2000 IFA titer by tenth day.

5) If the virus is administered to SD rat, an antibody is detected by 7th day after inoculation.

6) When this virus is cultured in Vero E6 cell, the plaque of about 0.3 cm can be obtained which is a much larger size compared with the case of other viruses.

The present invention provides a Hantaan virus vaccine which is prepared by culturing, proliferating, isolating and inactivating the novel virus.

The Hantaan virus vaccine of this prepared as follows: The Hantaan virus ROK84/105 strain which is isolated from the human body is administered as a seed to one-day-old suckling mice or rats, these mice or rats are raised for about 10 days, the heads thereof are cut apart after paralyzing of it to take the brain, the brain is treated with ethyl alcohol and protamine sulfate solution, the resultant is purified and inactivated, and an adjuvant is added to the final product.

In order to prepare the vaccine of the invention, the proliferation of the seed virus is required. For this purpose, the seed virus is diluted with BSS (balance salt solution) containing 1.0% bovine albumin, and the diluted virus solution is kept at 4° C., it being preferable to store at $-60°$ C. in the case of a long-term preservation.

The above-described diluted Hantaan virus solution was administered to the brains of suckling mice or rats. The average weight of mice after ten days of raising was 0.262 g and the titer of the antigen was 8,192 of the 20% brain suspension. Meanwhile, the average weight of the brains of the rats after 10 days of raising was 0.718g, and the titer of the antigen was 8,192 of the 20% brain suspension.

According to the present invention, the proliferation of the seed virus was high both in the mice and rats, but it seemed to be more desirable to proliferate it in rats. Upon proliferation of the virus, the mice die starting from 10th day after being paralyzed from 8th day, and the vaccine is prepared in such a manner that the brains just before decease are collected, their weight are measured, a 20%(W/V) solution is prepared with a dilution solution (PBS, pH 7.2) having the following composition, the contents are smashed by means of a cell crusher sufficiently, and the solution is subjected to a centrifugation at 3,000 rpm at 4° C. for 20 minutes to ultimately recover the supernatant.

| | |
|---|---|
| sodium chloride | 8.5 g |
| Sodium phosphate (monobasic).2H2O | 0.4 g |
| Sodium phosphate (dibasic).12H2O | 2.54 g |
| distilled water | to 1 L |

To the obtained supernatant, protamine sulfate solution is added to the supernatant, 30 to 40% cool ethanol is added in equivalent volume, and the mixture is left alone at 4° C. for 16 to 20 hours to precipitate viruses.

The above solution is subjected to a centrifugation at 3,000 rpm for 30 minutes to recover the precipitates, and the above dilution solution(PBS, pH 7.2) is added in the same amount as above to the precipitates. Then the mixture is sufficiently mixed in a blender, the viruses are extracted, centrifugation is carried out at 5,000 rpm for 30 minutes to recover the supernatant in the amount of 0.1 to 0.5 mg/ml, the solution is agitated for one to two hours, and the solution is subjected to a centrifugation at 5,000 rpm for 30 minutes to recover supernatant as a bulk.

The above bulk can be inactivated by means of ordinary method in the art such as formaldehyde treatment or heat treatment, and then, aluminium hydroxide gel is added in the amount of 500 ug/ml to obtain the desired vaccine.

In the above inactivation processes, in the case of where formaldehyde is used, a treatment with 0.01 to 0.05% suspension should be carried out for 15 days, while, if the heat treatment is to be employed, it is carried out at 60° C. for 30 minutes. In the former case, the temperature should be desirably kept below 4° C.

Having generally described the invention, a more complete understanding can be obtained by reference to certain specific examples, which are provided herein for purposes of illustration only and are not intended to be limiting unless otherwise specified.

EXAMPLES

The present invention will hereinafter be described by the following examples:

Example 1. Hantaan virus Vaccine (1) Preparation of Hantaan virus one-day-old suckling mice were administered with Hantaan virus ROK84/105 strain, were bred for 10 days, and the brains of the mice were cut apart after they were paralyzed. The brain collected emulsified by adding phosphate buffer (pH 7.2) in the amount of four fold on the basis of the brain weight, followed by centrifugation was carried out at 3,000 rpm for 20 minutes to recover the supernatant as virus solution. Then the lethal rate($LD_{50}$) of this virus solution was measured in order to know the infectivity, and $LD_{50}$ of the virus was $10^{9.68}$/ml, the measurement being carried out in the following order:

1) One-day-old suckling mice were taken.

2) The virus solution was subjected to step dilution by dilution buffer to $10^{-2}$ to $10^{-9}$.

3) The virus solutions in each step was administered into the brains of the suckling mice in the amount of 0.02 ml.

4) After injection, symptoms of mice were observed for 20 days, and the number of dead mice was recorded.

5) The concentration of dilution solution, which makes the number of the dead mice be a half to the administered mice, is sought.

6) After recognition of the desired concentration of dilution solution, the fatality ($LD_{50}$) is obtained, based on the Read and Muench Method.

The results thereof are shown in table 1 and 2 below.

TABLE 1

| Dilution ratio of virus solution (fold) | No. of inoculation | number of dead mice depending on rapse of days — Number of deceased: 1 | 2 | 3 | 4 | 5 | 6 | 7 | 8 | 9 | 10 | 11 | 12 | 13 | 14 | 15 | 16 | 17 | 18 | 19 | 20 | Fatality rate | Survival rate |
|---|---|---|---|---|---|---|---|---|---|---|---|---|---|---|---|---|---|---|---|---|---|---|---|
| $10^{-2}$ | 9 | 0 | 0 | 0 | 0 | 0 | 0 | 0 | 0 | 9 | | | | | | | | | | | | 9/9 | 0/9 |
| $10^{-3}$ | 13 | 0 | 0 | 0 | 0 | 0 | 0 | 13 | | | | | | | | | | | | | | 13/13 | 0/13 |
| $10^{-4}$ | 18 | 1 | 0 | 0 | 0 | 0 | 0 | 0 | 1 | 0 | 15 | 1 | | | | | | | | | | 17/17 | 0/17 |
| $10^{-5}$ | 16 | 0 | 1 | 0 | 0 | 0 | 0 | 0 | 0 | 2 | 6 | 6 | 1 | | | | | | | | | 15/15 | 0/15 |
| $10^{-6}$ | 13 | 0 | 0 | 0 | 0 | 0 | 0 | 0 | 0 | 1 | 7 | 2 | 2 | 0 | 0 | 0 | 0 | 0 | 0 | 0 | 0 | 12/13 | 1/13 |
| $10^{-7}$ | 14 | 1 | 0 | 0 | 0 | 0 | 0 | 0 | 0 | 0 | 0 | 0 | 0 | 0 | 1 | 1 | 2 | 1 | 0 | 0 | 0 | 5/13 | 8/13 |
| $10^{-8}$ | 9 | 0 | 0 | 0 | 0 | 0 | 0 | 0 | 0 | 0 | 1 | 0 | 1 | 0 | 1 | 0 | 0 | 0 | 0 | 0 | 0 | 3/9 | 6/9 |
| $10^{-9}$ | 23 | 0 | 0 | 0 | 0 | 0 | 0 | 0 | 0 | 0 | 0 | 0 | 0 | 0 | 0 | 0 | 2 | 1 | 1 | 0 | 0 | 4/23 | 19/23 |

(The number of deceased in a few day after inoculation is exempted as inoculation dead)

TABLE 2

| Dilution of virus solution (10 times $log_{10}$) | the fatality of mice ($LD_{50}$): deceased | survival | sum: total deceased | total survival | lethal rate: rate | % |
|---|---|---|---|---|---|---|
| −2 | 9 | 0 | 78 | 0 | 78/78 | 100 |
| −3 | 13 | 0 | 69 | 0 | 69/69 | 100 |
| −4 | 17 | 0 | 56 | 0 | 56/56 | 100 |
| −5 | 15 | 0 | 39 | 0 | 39/39 | 100 |
| −6 | 12 | 1 | 24 | 1 | 24/25 | 96 |
| −7 | 5 | 8 | 12 | 9 | 12/21 | 57 |
| −8 | 3 | 6 | 7 | 15 | 7/22 | 32 |
| −9 | 4 | 19 | 4 | 34 | 4/38 | 11 |

From the above table 2, $LD_{50}=10^{9.68}$/ml.

The antigen titer of the above virus solution was 8,192, which determined by the following method: The measurement was accomplished on the basis of EIA method by using polyvinyl bottom 96 well as the plate, and coating buffer(PBS) made by Sigma Diagnostics Co. as buffer dilution solution, washing buffer(PBS+0.1% tween 20), and dilution buffer(PBS+0.1% tween 20+2.5% bovine serum+0.1% thimerosal) as a buffer solution.

i) A plate coating was carried out by adding 100 ul portions of the goat anti-human IgM diluted to 500 folds with dilution buffer into each well of the plate and it was reacted at 4° for 16 to 20 hours. The total protein of the used goat anti-human IgM antibody, Product of Tago, Inc. was 1.15 mg/ml.

ii) The plate obtained from i) was washed three times with washing buffer, and the positive serum isolated from human body was diluted to be 16 units of EIA antibody titer. Thereafter, 100 ul portions of the above serum was poured into each well of the plate, and it was allowed to incubate at 37° C. for one hour.

iii) The plate reacted in ii) was washed three times with the washing buffer solution, 100 ul portions of the virus solution which was serially diluted to two folds of its concentration poured into the above each well of the plate, and the plate was incubated at 37° C. for one hour.

iv) This plate obtained from iii) was washed three times with the washing buffer solution. 100 ul portions of rabbit anti-hantaan antibody which was diluted to 3000 folds of its concentration with dilution buffer poured into each well of the plate, and it was incubated at 37° C. for one hour. At that time the EIA titer of rabbit anti-Hantaan antibody showed 4.

v) The plate obtained from iv) was washed three times, into each well of which 100 ul portions of Enzyme-conjugated anti-rabbit which was diluted to 100 folds of its concentration with the dilution buffer was poured, and incubated at 37° C. for one hour. The above enzyme conjugate, made by KPL company, which contains 0.1 mg of protein content and is a peroxidase labeled affinity purified antibody to human rabbit IgG, was used.

vi) The above plate was washed three times with the washing buffer. 100 ul portions of substrate was poured into each well of the plate, and it was incubated at 37° C. for 30 minutes. The used substrate, ABTS, was a combined solution of peroxidase substrate A [2,2-azino-dl-(3-ethyl-benzthiazoline)sulfonate) and peroxidase substrate solution B [hydrogen peroxide], mixing at a ratio of 1.1.

vii) The plate obtained from vi) was observed by ELISA detector at 405 nm to 415 nm of wavelength.

viii) The threshold value is obtaining by summing the arithmetic mean value of the known reference negative serum value with three folds of the standard deviation value thereof.

As a result, the titer of virus solution was 8,192.

(2) Treatment with ethanol

The above virus solutions were treated with various concentration of ethanol, i.e., 15%, 20%, 30% and 40%, and was allowed to stand at 4° C. for 16 to 20 hours, following by centrifugal separation at 12,000 rpm for 30 minutes to obtain EIA antigen titer of supernatant and sediment respectively. The results are shown in table 3 below. From this results, the optimum concentration of ethanol was selected.

TABLE 3

EIA antigen titer in each of ethanol concentration

| Concentration of ethanol | EIA titer precipitate | EIA titer supernatant |
|---|---|---|
| 15% | 1,024 | 16 |
| 20% | 1,024 | 8 |
| 30% | 1,024 | 4 |
| 40% | 1,024 | 4 |

After treatment with ethanol, virus solution was inactivated at 60° C. for 30 minutes, and was inoculated to rat to determine the relative antigenicity. The results are shown in table 4 below.

TABLE 4

Comparison of antigenicity after administration of ROK84/105 to rat.

| Inoculation | Animal | Route | Exp. No. | Immunofluorescent antibody 14th day | 21st day | 28th day |
|---|---|---|---|---|---|---|
| mouse brain virus | SD rat | 0.5 ml/IM | 1 | 16 | 64 | 32 |
| #3. ROK 84/105 |  |  | 2 | 64 | 64 | 64 |
| (MBV. 1% B.A) ethanol |  |  | 3 | 64 | 64 | 64 |
| 15% 60° C. 30' |  |  | 4 | 16 | 64 | 64 |
| #3. ROK 84/105 | " | " | 1 | 64 | 256 | 256 |
| (MBV. 1% B.A) ethanol |  |  | 2 | 256 | 256 | 256 |
| 20% 60° C. 30' |  |  | 3 | 256 | 256 | 256 |
|  |  |  | 4 | 128 | 256 | 1024 |
| #3. ROK 84/105 | " | " | 1 | 256 | 1024 | 1024 |
| (MBV. 1% B.A) ethanol |  |  | 2 | 1024 | 1024 | 4096 |
| 30% 60° C. 30' |  |  | 3 | 256 | 1024 | 1024 |
|  |  |  | 4 | 256 | 1024 | 1024 |
| #3. ROK 84/105 | " | " | 1 | 512 | 1024 | 1024 |
| (MBV. 1% B.A) ethanol |  |  | 2 | 256 | 1024 | 1024 |
| 40% 60° C. 30' |  |  | 3 | 1024 | 1024 | 1024 |
|  |  |  | 4 | 256 | 512 | 1024 |

TABLE 5

Immunofluorescent Antibody value when virus solution treated with ethanol and inactivated at 60° C. for 30 min. was administered to rat.

| Concentration of ethanol | Antibody titer of rat after immunity (IFA) 14th day | 21st day | 28th day |
|---|---|---|---|
| 15% | 32 | 64 | 64 |
| 20% | 128 | 256 | 512 |
| 30% | 512 | 1,024 | 2,048 |
| 40% | 512 | 512 | 256 |

As shown in table 3, 4 and 5, 30% of ethanol concentration revealed the most excellent yield of antigen and antibody production. Accordingly, it is preferably to treat the virus solution with 30% of ethanol.

(3) Treatment with Protamine Sulfate

The virus solution treated with the above ethanol was treated with the various concentrations of protamine sulfate to select the optimum concentration thereof.

Figure 1:
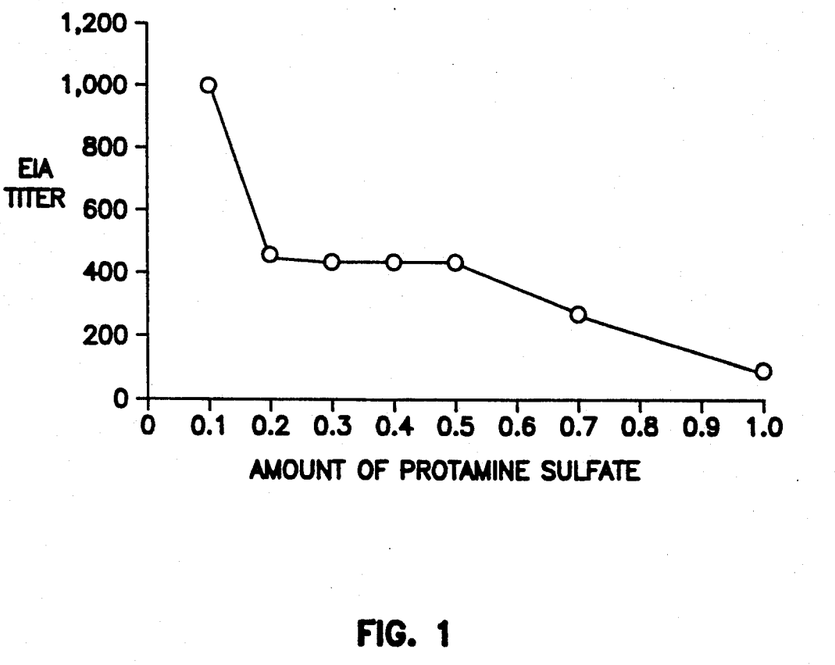
FIG. 1 is a drawing showing the results obtained EIA antigen titer of supernatant depending on the amount of the application of protamine sulfate, in the example 1 of this invention.

That is, the virus solution treated with ethanol was respectively treated with the concentrations of protamine sulfate, 0.1 mg/ml, 0.2 mg/ml, 0.3 mg/ml, 0.4 mg/ml, 0.7 mg/ml and 1.0 mg/ml, was allowed to stand at 4° C. for 2 hours, the virus solution was subjected to centrifugation at 18,000 rpm for 30 minutes, and the EIA antigen titer of supernatant was determined. The results are shown in FIG. 1.

(4) Inactivation step

The above virus solution was treated with formalin 0.05%, and then fatality ($LD_{50}$) together with infection rate($ID_{50}$) were observed depending on the lapse of days, when it was inoculated.

Figure 2:
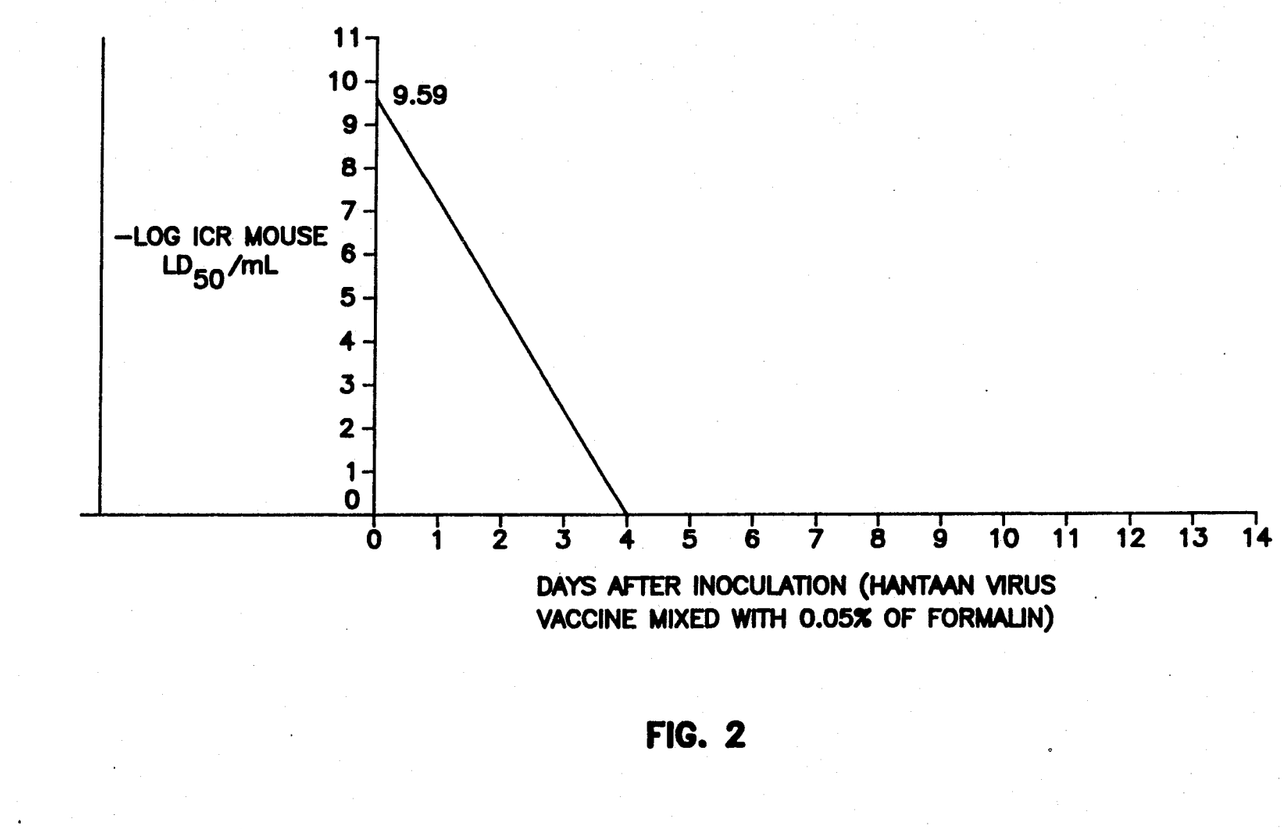
FIG. 2 is a drawing showing the Lethal Rate($LD_{50}$) of mouse depending on the application of Hantaan virus.
Figure 3:
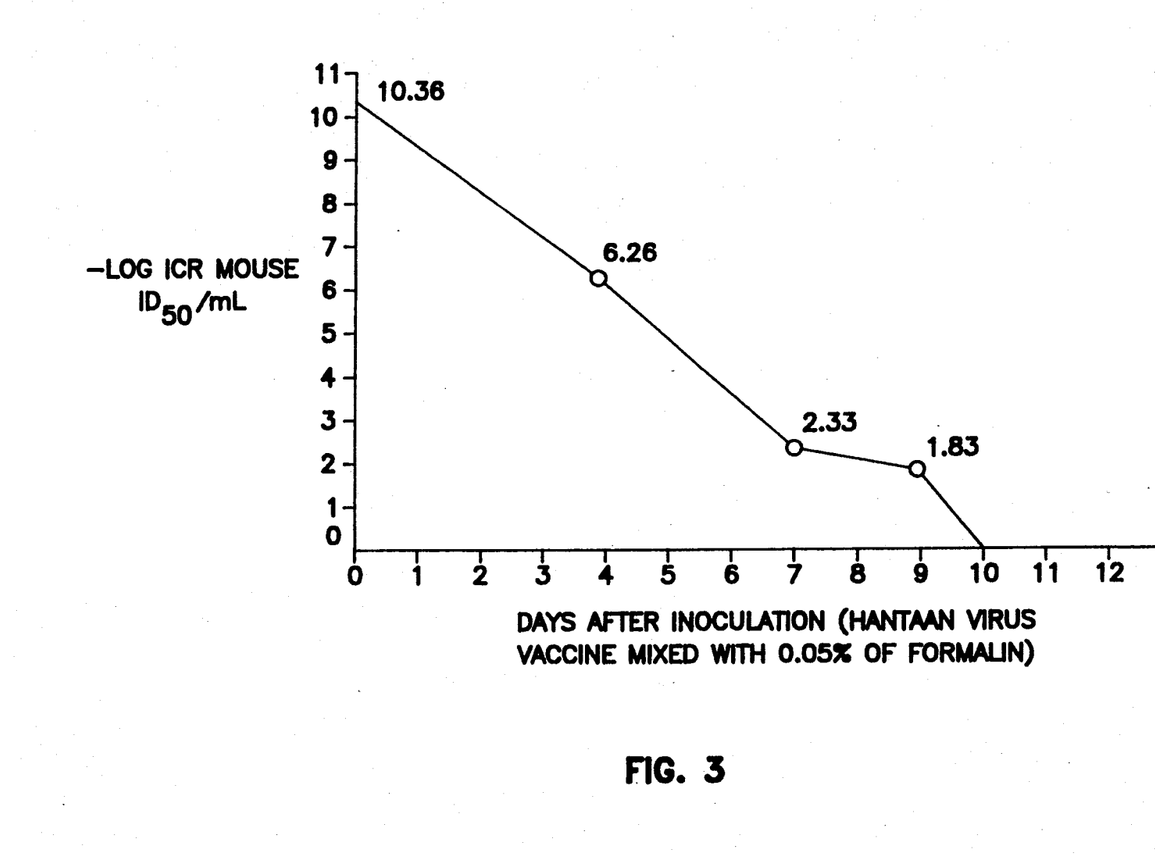
FIG. 3 is a drawing showing the Infection Rate($ID_{50}$) of mouse in accordance with the periods of the treatment of formalin to the Hantaan virus.

The virus solution just after treating with formalin, fourth day, seventh day, ninth day and tenth day, which is serially diluted to ten folds, was inoculated with one-day-old suckling mice respectively. The fatalities of the mice according to each concentration are shown in Table 6 below, the fatality of mice is shown in FIG. 2 and infection rate is shown in FIG. 3.

with formalin for more than 10 days was administered to the brains of mice, there was no deceased mouse. After 30 days from administration, the heads of mice was cut apart to take the brain and it was observed whether the virus infected by means of the indirect immunofluorescent assay. As the result of this, the virus infection was not detected. Accordingly, it is confirmed that the Hantaan virus ROK84/105 of the present invention was to be inactivated.

(5) Process for Treatment of Adjuvant

Aluminium hydroxide gel was added as an adjuvant into the Hantaan virus ROK84/105 of the present invention inactivated with formalin, and it as incubated at 4° C. for 15 days. The resulted solution was injected to rats via intramuscular in an amount of 0.5 ml/rat to detect the titer of EIA antibody.

Figure 4:
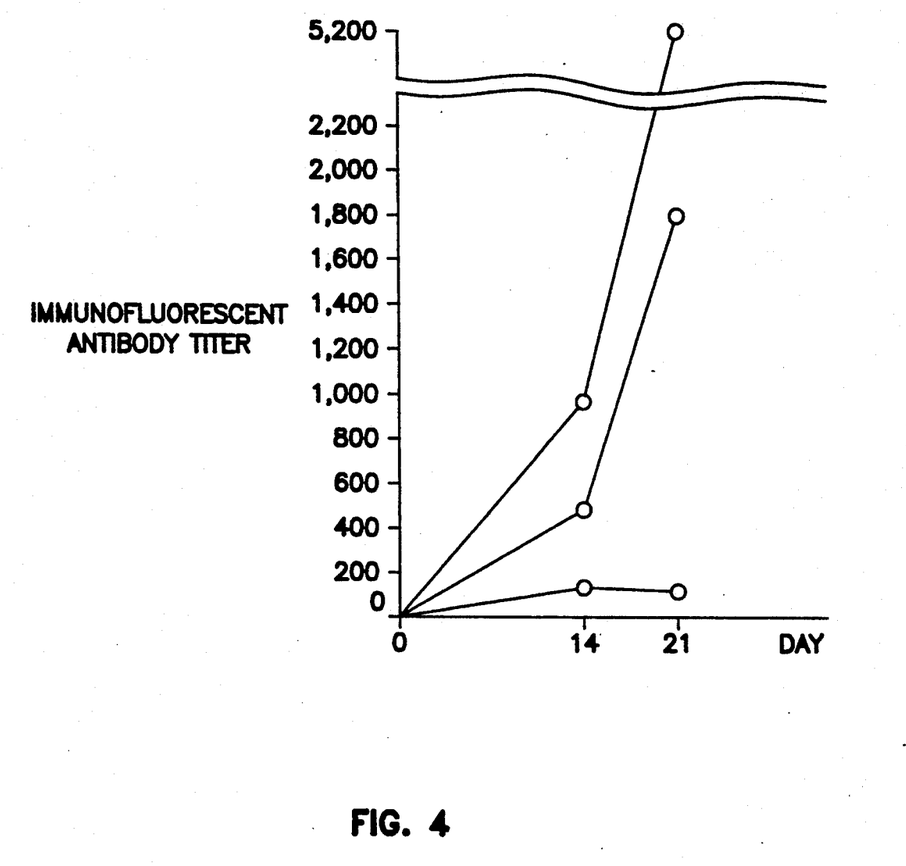
FIG. 4 is a drawing showing the production of immunofluorescent entity(IF) depending on the amount of Adjuvant.
Figure 5:
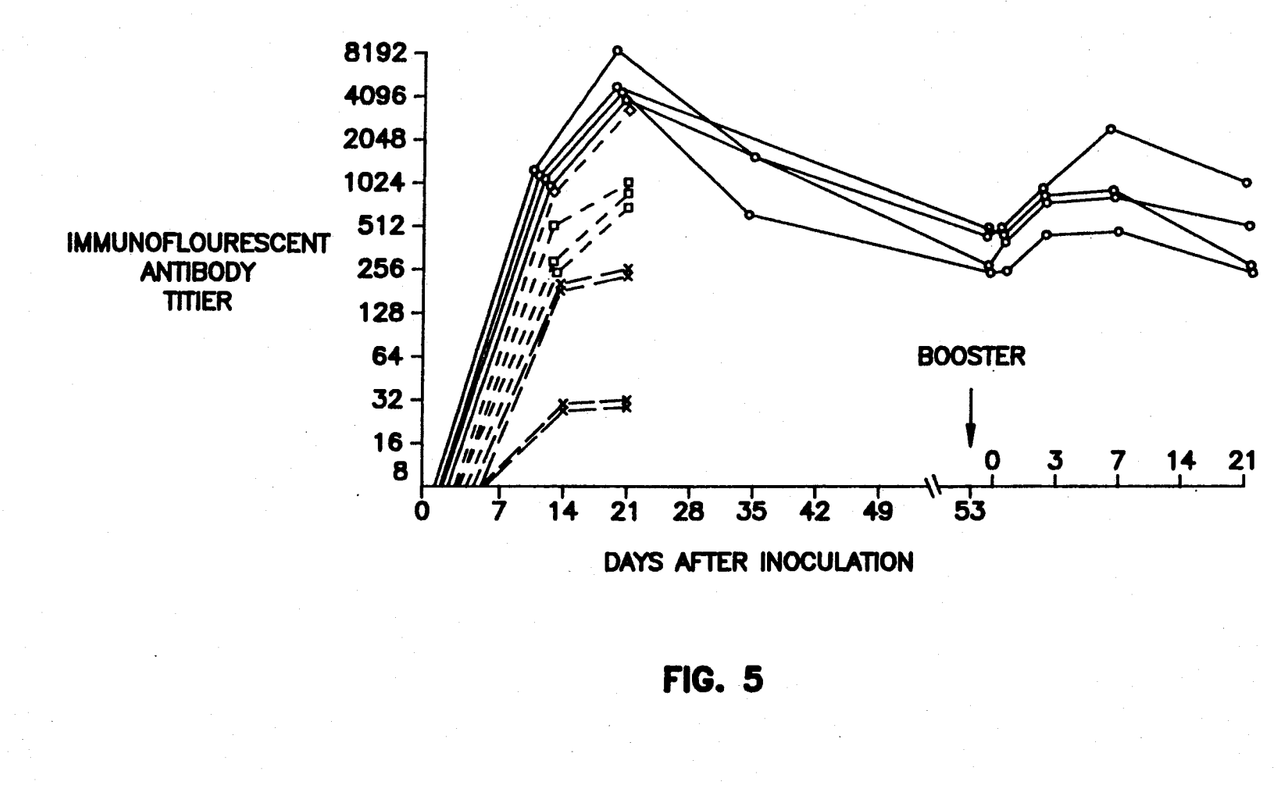
FIG. 5 is a drawing showing the production of immunofluorescent antibody depending on the amount of aluminium hydroxide to rats vaccinated with ROK84/105(MBV) absorbed to aluminium hydroxide gel.

The results are shown in Table 8, Table 9, FIG. 4 and FIG. 5.

TABLE 8

| Day | Dilution (fold) | No. of inoculation | Deceased | Infected | $LD_{50/0.02\ ml}$ | $LD_{50/1.0\ ml}$ | $ID_{50/0.02\ ml}$ | $ID_{50/1.0\ ml}$ |
|---|---|---|---|---|---|---|---|---|
| 0 | $10^{-5}$ | 18 | 18 | 18 | $10^{-7.89}$ | $10^{-9.59}$ | $10^{-8.66}$ | $100^{-10.36}$ |
|  | $10^{-6}$ | 19 | 19 | 19 |  |  |  |  |
|  | $10^{-7}$ | 18 | 18 | 18 |  |  |  |  |
|  | $10^{-8}$ | 8 | 3 | 5 |  |  |  |  |
|  | $10^{-9}$ | 5 | 1 | 3 |  |  |  |  |
|  | $10^{-10}$ | 7 | 0 | 0 |  |  |  |  |
| 4 | $10^{0}$ | 9 | 0 | 9 | 0 | 0 | $10^{-4.56}$ | $10^{-6.26}$ |
|  | $10^{-1}$ | 9 | 0 | 9 |  |  |  |  |
|  | $10^{-2}$ | 10 | 0 | 10 |  |  |  |  |
|  | $10^{-3}$ | 11 | 0 | 11 |  |  |  |  |
|  | $10^{-4}$ | 10 | 0 | 8 |  |  |  |  |
|  | $10^{-5}$ | 11 |  | 3 |  |  |  |  |
| 7 | $10^{0}$ | 9 | 0 | 9 | 0 | 0 | $10^{-0.63}$ | $10^{-2.33}$ |
|  | $10^{-1}$ | 10 | 0 | 2 |  |  |  |  |
| 9 | $10^{0}$ | 20 | 0 | 11 | 0 | 0 | $10^{-0.13}$ | $10^{-1.83}$ |
|  | $10^{-1}$ | 11 | 0 | 1 |  |  |  |  |
| 10 | 0 | 12 | 0 | 0 |  |  |  |  |
|  | $10^{-1}$ | 11 | 0 | 0 |  |  |  |  |
| 14 | 0 | 9 | 0 | 0 |  |  |  |  |
|  | $10^{-1}$ | 10 | 0 | 0 |  |  |  |  |

As shown in FIG. 2 and 3, the Hantaan virus of the invention inactivated with formalin 0.05% for more than 10 days does not show infection. And when the Hantaan virus of this invention inactivated with formalin 0.05% for 14 days was administered to rats, the antigenicity to the above virus solution was observed, and the results are shown in Table 7 below.

TABLE 7

Antigenicity of ROK84/105 (MBV) strain injected to rats.

| Inoculation ROK 84/105 (MBV) | Animal | Route | Exp. No. | Immunofluorescent antibody |  |
|---|---|---|---|---|---|
|  |  |  |  | 21st day | 28th day |
| ROK 84/105 (MBV) formalin (treatment) for 14 days) | SD rat | 0.5 ml/IM | 1 | 256 | 256 |
|  |  |  | 3 | 64 | 128 |
|  |  |  | 4 | 128 | 256 |

The titer of EIA antibody after treatment of adjuvant

|  | EIA titer (supernatant) | | |
|---|---|---|---|
|  | 3rd day | 7th day | 15th day |
| control | 2,048 | 2,048 | 2,048 |
| aluminium hydroxide gel (250 μg/ml) | 2,048 | 1,024 | 512 |
| aluminium hydroxide gel (250 μg/ml) | 2,048 | 512 | 16 |

As understood from table 6 and 7, when the Hantaan virus ROK84/105 of the present invention inactivated

TABLE 9 antigenicity after administering aluminium gel-adsorbed ROK84/105 (MBV)

| Inoculation | Animal | Route | Exp. No. | Immunofluorescent antibody value | | |
|---|---|---|---|---|---|---|
|  |  |  |  | 14th day | 21st day | 35th day |
| #3. ROK 84/105(MBV) formalin aluminium gel 500 μg/ml | SD rat | 0.5 ml/IM | 1 | 1024 | 4096 | 1024 |
|  |  |  | 2 | 1024 | 8192 | 1024 |
|  |  |  | 3 | 1024 | 4096 | 512 |

TABLE 9-continued

| | antigenicity after administering aluminium gel-adsorbed ROK84/105 (MBV) | | | | | |
|---|---|---|---|---|---|---|
| | | | | Immunofluorescent antibody value | | |
| Inoculation | Animal | Route | Exp. No. | 14th day | 21st day | 35th day |
| | | | 4 | 1024 | 4096 | 1024 |
| #3. ROK 84/105(MVB) aluminium gel 250 μg/ml | " | " | 1 | 256 | 1024 | 128 |
| | | | 2 | 1024 | 4096 | 256 |
| | | | 3 | 256 | 1024 | 512 |
| | | | 4 | 512 | 1024 | 512 |
| #3. ROK 84/105(MBV) formalin(control) | " | " | 1 | 256 | 256 | 256 |
| | | | 2 | 32 | 32 | 32 |
| | | | 3 | 32 | 32 | 32 |
| | | | 4 | 256 | 256 | 128 |

From the above Table 8, Table 9, FIG. 3 and FIG. 4, it is understood that it is the most satisfactory method to treat the Hantaan virus ROK84/105 of this invention with 500 ug/ml of Aluminium gel for the production of antibody. experiment 1. Test of Hantann virus Vaccine to animal (1) Experiment for determination of dose in the rate The Hantaan virus vaccine prepared from the above Example 1 was administered to rats with various kinds of EIA antigen titer, thereby determining the optimum dose of vaccine.

After rats were subjected to be immunized with the Hantaan virus vaccine of the present invention, the level of antibody production depending on lapse of days was measured by the indirect immunofluorescence assay. The Hantaan virus vaccine was injected via intramuscular to rats. The results of antibody reaction are shown in Table 10.

TABLE 10

Determination of Dose of Hantaan virus vaccine by intramuscular injection to rats.

| group | Titer of antigen (ELISA) | No. of rat | antibody titer of rat after vaccine inoculation | | |
|---|---|---|---|---|---|
| | | | 12th day | 21st day | 28th day |
| 1 | 4,096 | 1 | 512 | 2,048 | 2,048 |
| | | 2 | 512 | 2,048 | 2,048 |
| | | 3 | 512 | 1,024 | 1,024 |
| | | 4 | 512 | 2,048 | 2,048 |
| 2 | 2,048 | 1 | 512 | 512 | 1,024 |
| | | 2 | 512 | 1,024 | 1,024 |
| | | 3 | 512 | 1,024 | 1,024 |
| | | 4 | 512 | 2,048 | 2,048 |
| 3 | 1,024 | 1 | 512 | 1,024 | 1,024 |
| | | 2 | 256 | 512 | 1,024 |
| | | 3 | 512 | 1,024 | 1,024 |
| | | 4 | 512 | 2,048 | 1,024 |
| 4 | 512 | 1 | 32 | 128 | 128 |
| | | 2 | 512 | 1,024 | 1,024 |
| | | 3 | 32 | 32 | 32 |
| | | 4 | 128 | 256 | 256 |
| 5 | 256 | 1 | — | | |
| | | 2 | — | | |
| | | 3 | — | | |
| | | 4 | — | | |
| 6 | 128 | 1 | — | | |
| | | 2 | — | | |
| | | 3 | — | | |
| | | 4 | — | | |

As shown in Table 10, it is confirmed that antibody was produced when more than 512 EIA titer of the vaccine of the invention was inoculated.

(2) Antibody-booster experiment.

It is found that when the vaccine of this invention was primarily injected to rat, antibody was increasingly produced till one month, and then it was decreased. The additional inoculation between 45 and 60 days makes remarkably antibody be produce. The results are depicted in FIG. 5.

(3) Safety Experiment of Hantaan virus vaccine.

In order to test safety of the vaccine of the invention, 0.2 ml portions of the vaccine were inoculated to the brains of suckling mice, and the health condition of mice were observed for 30 days. 30 days later, the heads of mice were cut apart to collect brains, which are prepared to the tissue plate by cutting the above at a size of 0.4 um at −30° C. in Cryostat. After the said tissue plate was fixed with acetone, it was primarily reacted with 16 units/drop of the patient's serum of hemorrhagic fever, and was secondarily reacted with 8 units/drop FITC-conjugated anti-human gamma-globulin to observe proliferation of virus by means of the fluorescence microscope, thereupon proliferation was not recognized in the brains. The above brains of mice were emulsified to be 20% thereof and then the resulted emulsion was inoculated to the brains of suckling mice. As a result of checking the multiplication of virus by the above method, the proliferation of virus was not detected. Accordingly, the Hantaan virus vaccine of the invention was determined to be completely inactivated and proved to be detoxicated.

What we claimed is:

1. A vaccine for Hantaan virus which is prepared by a process comprising the steps of introducing Hantaan virus strain ROK 84/105 into a rat or mouse, subsequently removing brain tissue from the brain of the rat or mouse, extracting the brain tissue with an extraction fluid, purifiying the resulting virus extract, and inactivating the virus in the resulting virus extract, wherein Hantaan virus strain ROK 84/105 is a strain of Hantaan virus having an international deposit number of ATCC VR 2250.

2. The Hantaan virus vaccine as claimed in claim 1 wherein, the step of purifying is carried out with 30 to 40% of ethyl alcohol.

3. The Hantaan virus as claimed in claim 1 wherein, said step of purifying is carried out with 0.1 to 0.5 mg/ml of protamine sulfate.

4. The Hantaan virus vaccine as claimed in claim 1, wherein said inactivation step is carried out by adding formalin to the resulting virus extract in an amount sufficient to equal 0.01 of the 0.05% basis to total amount, and allowing the resulting extract to stand at 4° C. for at least 10 days.

5. The Hantaan virus vaccine as claimed in claim 1, wherein said inactivation step is carried out by heat treatment at 60° C. for 30 minutes.

6. The Hantaan virus vaccine as claimed in claim 1, wherein said mouse or rat is a one-day-old suckling mouse or rat.

7. The Hantaan virus vaccine as claimed in claim 1, wherein said step of subsequently removing occurs at least 10 days after the step of introducing.

8. The Hantaan virus vaccine as claimed in claim 1, wherein the step of introducing includes injecting the virus into the mouse or rat, and wherein the step of subsequently removing includes paralyzing the mouse or rat, cutting apart the head of the mouse or rat and removing brain tissue from the brain of the mouse or rat.

9. The Hantaan virus vaccine as claimed in claim 1, wherein said process further includes the step of adding an adjuvant to the virus extract following the step of inactivating the virus contained therein.

10. A viral vaccine comprising a plurality of virion particles, said plurality of virion particles being Hantaan virus particles of the strain ROK 84/105 and having an International Deposit Number of ATCC VR 2250.

11. The viral vaccine as claimed in claim 10, said vaccine further comprising an adjuvant, wherein said plurality of virion particles are inactivated.

12. A viral vaccine comprising a plurality of virion particles, said plurality of virion particles being Hantaan virus particles of the strain ROK 84/105 having an international deposit number of ATCC VR 2250, wherein each of said plurality of Hantaan virus virion particles include: a single strand of RNA having a plurality of definable segments, said RNA strand including at least one negative-sense RNA genome, each of said plurality of virion particles having a spherical or an ellipsoid shape having a diameter of about 95 nm, a lipoprotein envelope enclosing a plurality of nucleocapsids, and a plurality of fibers extending outwardly from said envelope a distance of about 5–10 nm, and wherein the titer of the virus in Vero E6 cells is $10^{7.2}$/ml.

13. The viral vaccine of claim 12, said RNA strand having three definable segments and a plurality of negative-sense RNA genomes, each of said virion particles having a total molecular weight of about $4.5 \times 10^6$ and three viral nucleocapsids.

14. The viral vaccine of claim 13 wherein a titer of the Hantaan virus in the brain of a suckling mouse is about $10^{9.8}$/ml, a titer of the Hantaan virus in the brain of a suckling rat is about $10^{9.3}$/ml, and an antigen titer of the Hantaan virus is about 8,000 to about 8,200.

15. The viral vaccine of claim 14 further comprising an adjuvant.

* * * * *

UNITED STATES PATENT AND TRADEMARK OFFICE
CERTIFICATE OF CORRECTION

PATENT NO. : 5,183,658

DATED : February 2, 1993

INVENTOR(S) : Ho W. Lee et al.

Page 1 of 3

It is certified that error appears in the above-identified patent and that said Letters Patent is hereby corrected as shown below:

At column 2, line 68, after "Seoul" delete "(".

At column 4, line 3, for "4" read --4.--.

At column 4, line 33, after "this" insert --invention is--.

At column 5, line 8, after "ethanol" insert --in PBS (ethanol:PBS=4:6)--.

At column 7, line 59, after "to" delete "human".

At column 8, line 63, for "preferably" read --preferable--.

At column 9, line 21, after "Fig. 3" insert --Table 6. Fatality ($LD_{50}$) and infection rate ($ID_{50}$) of mouse depending on lapse of days--.

At column 10, line 13, for "as" read --was--.

At column 10, lines 19-20, delete "TABLE 8".

At column 10, line 41, above "The titer of EIA antibody after treatment of adjuvant" insert --TABLE 8--.

At column 11, line 8, for "(MVB)" read --(MBV)--.

UNITED STATES PATENT AND TRADEMARK OFFICE
CERTIFICATE OF CORRECTION

PATENT NO. : 5,183,658  Page 2 of 3
DATED : February 2, 1993
INVENTOR(S) : Ho W. Lee et al.

It is certified that error appears in the above-identified patent and that said Letters Patent is hereby corrected as shown below:

At column 9 and 10, line 20 delete for

| Day | *Dilution | No. of inoculation | Deceased | Infected | $LD_{50}$/ 0.02ml | $LD_{50}$/ 1.0ml | $ID_{50}$/ 0.02ml | $ID_{50}$/ 1.0ml |
|---|---|---|---|---|---|---|---|---|
| 0 | $10^{-5}$ | 18 | 18 | 18 | $10^{-7.89}$ | $10^{-7.59}$ | $10^{-8.44}$ | $100^{-10.16}$ |
|   | $10^{-6}$ | 19 | 19 | 19 | | | | |
|   | $10^{-7}$ | 18 | 18 | 18 | | | | |
|   | $10^{-8}$ | 8  | 3  | 5  | | | | |
|   | $10^{-9}$ | 5  | 1  | 3  | | | | |
|   | $10^{-10}$| 7  | 0  | 0  | | | | |
| 4 | $10^{0}$  | 9  | 0  | 9  | 0 | 0 | $10^{-4.54}$ | $10^{-6.24}$ |
|   | $10^{-1}$ | 9  | 0  | 9  | | | | |
|   | $10^{-2}$ | 10 | 0  | 10 | | | | |
|   | $10^{-3}$ | 11 | 0  | 11 | | | | |
|   | $10^{-4}$ | 10 | 0  | 8  | | | | |
|   | $10^{-5}$ | 11 |    | 3  | | | | |
| 7 | $10^{0}$  | 9  | 0  | 9  | 0 | 0 | $10^{-0.63}$ | $10^{-2.31}$ |
|   | $10^{-1}$ | 10 | 0  | 2  | | | | |
| 9 | $10^{0}$  | 20 | 0  | 11 | 0 | 0 | $10^{-0.13}$ | $10^{-1.85}$ |
|   | $10^{-1}$ | 11 | 0  | 1  | | | | |
|   | 0         | 12 | 0  | 0  | 0 | | | |
|   | $10^{-1}$ | 11 | 0  | 0  | | | | |
| 14| 0         | 9  | 0  | 0  | | | | |
|   | $10^{-1}$ | 10 | 0  | 0  | | | | | read

| Day | Dilution (fold) | No. of inoculation | Deceased | Infected | $LD_{50}$/ 0.02ml | $LD_{50}$/ 1.0ml | $ID_{50}$/ 0.02ml | $ID_{50}$/ 1.0ml |
|---|---|---|---|---|---|---|---|---|
| 0 | $10^{-5}$ | 18 | 18 | 18 | | | | |
|   | $10^{-6}$ | 19 | 19 | 19 | | | | |
|   | $10^{-7}$ | 18 | 18 | 18 | $10^{-7.89}$ | $10^{-7.59}$ | $10^{-8.44}$ | $100^{-10.36}$ |
|   | $10^{-8}$ | 8  | 3  | 5  | | | | |
|   | $10^{-9}$ | 5  | 1  | 3  | | | | |
|   | $10^{-10}$| 7  | 0  | 0  | | | | |
| 4 | $10^{0}$  | 9  | 0  | 9  | | | | |
|   | $10^{-1}$ | 9  | 0  | 9  | | | | |
|   | $10^{-2}$ | 10 | 0  | 10 | | | | |
|   | $10^{-3}$ | 11 | 0  | 11 | 0 | 0 | $10^{-4.54}$ | $10^{-6.24}$ |
|   | $10^{-4}$ | 10 | 0  | 8  | | | | |
|   | $10^{-5}$ | 11 |    | 3  | | | | |
| 7 | $10^{0}$  | 9  | 0  | 9  | 0 | 0 | $10^{-0.63}$ | $10^{-2.31}$ |
|   | $10^{-1}$ | 10 | 0  | 2  | | | | |
| 9 | $10^{0}$  | 20 | 0  | 11 | 0 | 0 | $10^{-0.13}$ | $10^{-1.81}$ |
|   | $10^{-1}$ | 11 | 0  | 1  | | | | |
| 10| $10^{0}$  | 12 | 0  | 0  | | | | |
|   | $10^{-1}$ | 11 | 0  | 0  | | | | |
| 14| $10^{0}$  | 9  | 0  | 0  | | | | |
|   | $10^{-1}$ | 10 | 0  | 0  | | | | |

--.

UNITED STATES PATENT AND TRADEMARK OFFICE
CERTIFICATE OF CORRECTION

PATENT NO. : 5,183,658

DATED : February 2, 1993

INVENTOR(S) : Ho W. Lee et al.

It is certified that error appears in the above-identified patent and that said Letters Patent is hereby corrected as shown below:

At column 11, line 20, for "Hantann" read --Hantaan--.

In claim 4, at column 12, line 63, for "0.05%" read --0.5%--.

Signed and Sealed this

Twenty-sixth Day of April, 1994

*Attest:*

BRUCE LEHMAN

*Attesting Officer*      *Commissioner of Patents and Trademarks*